United States Patent [19]

Stevens et al.

[11] 4,403,687
[45] Sep. 13, 1983

[54] LINKABLE SAMPLE-TUBE CARRYING TRAY WITH TABS AND GEARS

[75] Inventors: William M. Stevens, Loveland; Eugene L. Timperman, Cincinnati, both of Ohio

[73] Assignee: Randam Electronics, Inc., Cincinnati, Ohio

[21] Appl. No.: 201,190

[22] Filed: Oct. 27, 1980

[51] Int. Cl.³ .............................................. B65G 37/00
[52] U.S. Cl. .................................... 198/472; 206/558; 206/561
[58] Field of Search ............... 198/472, 648, 580, 780; 206/561, 558; 220/21, 23.4; 250/328; 238/10 E, 10 F; 213/182–184, 75 R

[56] References Cited
U.S. PATENT DOCUMENTS

| 2,701,635 | 2/1955 | Mills | 206/561 X |
| 3,643,812 | 2/1972 | Mander et al. | 206/558 X |
| 3,647,105 | 3/1972 | Keeslar | 206/561 X |
| 3,844,428 | 10/1974 | Olsen | 198/472 X |

Primary Examiner—Robert C. Watson
Assistant Examiner—Douglas D. Watts
Attorney, Agent, or Firm—Eugene F. Friedman

[57] ABSTRACT

A sample tray carrying a two-dimensional array of sample tubes for analyses by an instrument. Tabs on the side of the tray inform the instrument as to the location of the rows of sample tubes within the tray. A short wide rack gear followed by two long thin rack gears cooperate with a pinion gear on the instrument to move the sample tray along a channel established by the instrument. The wide short rack gear serves to properly orient the tray in the instrument's channel. A C-hook at the rear of one tray can engage a T-tab at the front of a following tray to couple the two trays together. The coupling components do not extend below the upper half of the tray to assist the operator when coupling two trays together. Overhanging rack gear segments between the two coupled trays allow for their continuous propulsion by the instrument's cooperating pinion gear. The tray may take the form of a hollow shell into which fit holders providing the actual locations for the sample tubes. The holder may have a composition of plastic, cardboard, or styrofoam. Alternatively, the tray may have a nonremovable holder and operate as a solid unit.

33 Claims, 12 Drawing Figures

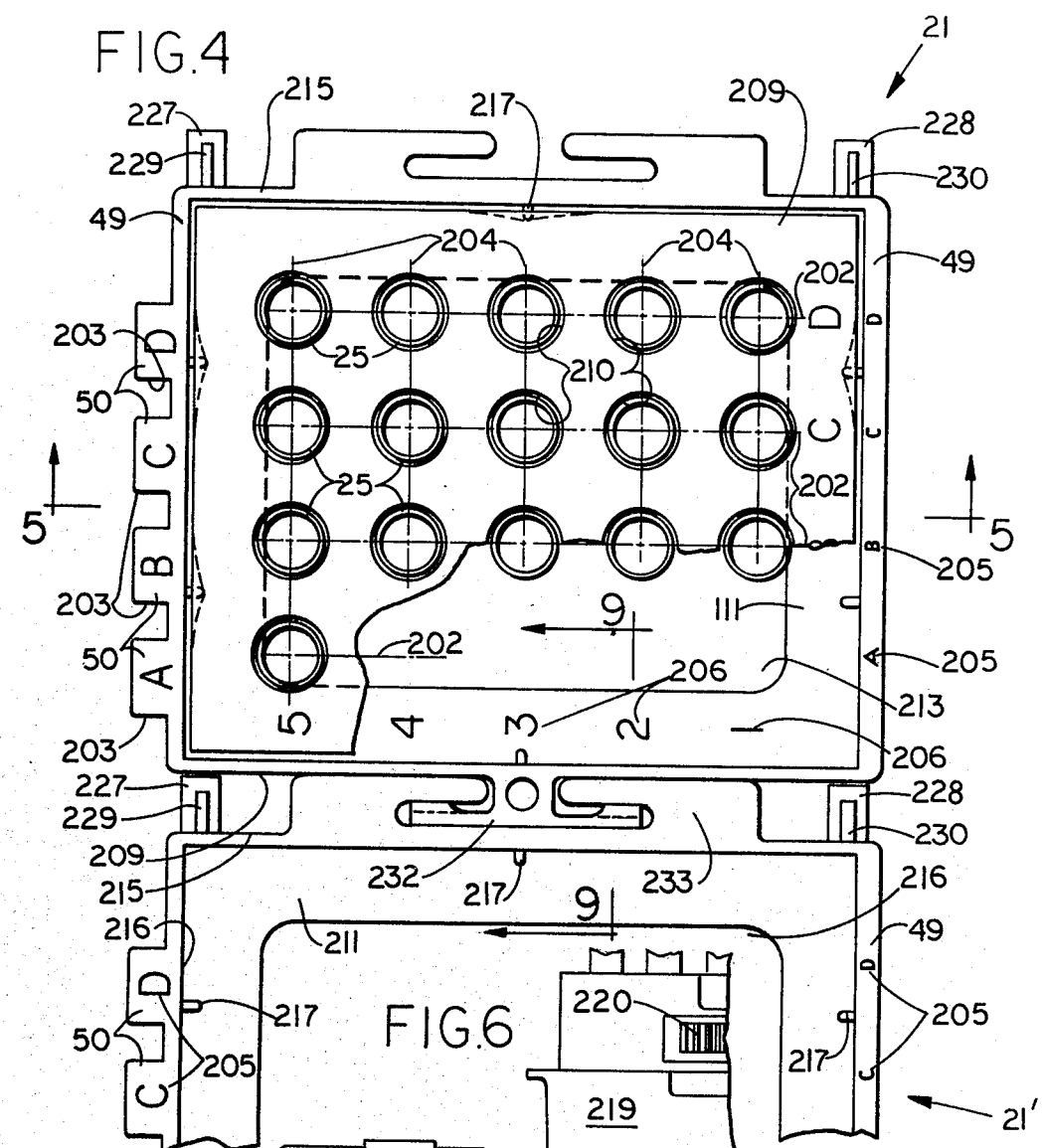

LINKABLE SAMPLE-TUBE CARRYING TRAY WITH TABS AND GEARS

CROSS REFERENCE TO RELATED APPLICATIONS

The present application relates to the U.S. utility patent applications "Analytical Instrument with Two Moving Trains of Sample Holder-Carrying Trays Under Microprocessor Control" by William M. Stevens, Ser. No. 200,895, filed Oct. 27, 1980, and "Calibration with Double-Pass Measurements and Computational Peak Finding" by William E. Atkinson, William J. Dirr, and William M. Stevens, Ser. No. 200,887, filed Oct. 27, 1980, and design patent application "Carrying Tray for Sample Tubes" by William M. Stevens and Eugene L. Timperman, Ser. No. 200,889, filed Oct. 27, 1980. The present application has the same filing date as the cited applications and incorporates their disclosures.

BACKGROUND

Analytical instruments have found use in modern laboratories for performing a large number of routine analyses. Accordingly, such instruments require the handling and processing of a large number of samples during a day of typical use. Quite often, the samples assume a liquid form. Accordingly, they and their containers must receive careful handling in order to avoid the loss of the samples themselves and the possible contamination of their surrounding environs. The latter becomes a particularly egregious problem where the sample contains radioactive or infectious material.

An operator's manual insertion of a sample tube into an instrument immediately prior to its analysis and its removal immediately afterwards has proven very inefficient. Initially, it requires the constant and total attention of an operator. The expenditure for such an individual immediately imposes a heavy economic burden upon the running of each essay.

Furthermore, the operator simply cannot replace an assayed sample with an unknown sample in the instrument with much speed. Consequently, the efficiency of the instrument, which must sit idle while waiting for the next sample, suffers further.

Additionally, replacing sample tubes in the instrument represents a boring, unchallenging task. As a result, the operator may not devote his full attention to its proper performance. Consequently, the very nature of the effort required of the operator may lead to its incorrect performance with concomitant inaccurate and possibly seriously deleterious results.

Thus, many instruments have undertaken to automatically handle a multitude of sample holders in addition to their more usual performance of particular analyses upon the samples. Some of these sample-changing instruments attempt to handle a number of sample holders placed individually into a retaining device. The device then subsequently moves the individual samples to the instrument's detector. These instruments which accept only individual sample tubes have only limited capacity. They also continue to require substantial attention because of the necessity of handling each of the sample tubes going into the instrument. Lastly, they incorporate complicated mechanisms for receiving, holding, and moving the individual sample tubes.

In an effort to achieve greater efficiency, other instruments have attempted to receive and operate upon trays each carrying a multitude of sample holders. However, the instrument becomes limited by the necessity of determining the position of the sample tubes within the trays themselves. Thus, they must first achieve relative motion between the detector in the instrument and the trays. They must also properly locate the sample tubes relative to the exterior configuration of the trays.

The sample trays in these instruments remain totally passive. They do not assist the instrument in the proper location of the tubes relative to the detector. As a result, the instruments must incorporate sufficient and sufficiently sophisticated components to bring the sample tubes and the detector together. These trays provide very little if any assistance in this endeavor.

Furthermore, the trays for a particular instrument can possess very little degree of variability from each other. Any change in their configuration will very likely confuse the instrument and hinder, if not absolutely prevent, the proper handling of the sample tubes inside the tray.

As examples of such sample trays, the U.S. Pat. Nos. 3,062,764 to W. W. Allen et al.; 3,859,528 to S. H. Luitwieler, Jr., et al; and 4,040,533 to W. J. De Boer all show sample trays having a one-dimensional array of tubes. The instrument attempts to move the trays along various paths on the top of a flat table in order to bring the sample tubes to the detector.

O. G. H. Junger et al., in U.S. Pat. No. 3,327,833, goes a step further and moves such sample trays vertically as well as horizontally. As with the prior patents, the trays all have the same configuration in order to permit the instrument to handle them properly.

L. E. Packard et al., in their U.S. Pat. No. 3,257,561, incorporates circular trays having sample tubes at their peripheries. The patent then discloses an extremely complex mechanism for shifting each tray from one stack of unanalyzed samples to another stack after the testing procedure.

Further, U.S. Pat. Nos. 3,855,473 to J. E. Burgess et al. and 3,911,274 to C. J. Roos et al. show instruments utilizing trays with two-dimensional arrays of sample tubes. However, the trays remain motionless and require the detector, in both instruments, to have two degrees of freedom of motion in order to find the sample tubes. The trays in the former of the two patents have absolute regularity for this purpose. In the latter case, the operator may place strips of light sources on the instrument itself to help it find the tubes within the trays.

J. S. Hof et al.'s U.S. Pat. No. 3,654,472 places trays with two-dimensional arrays of tubes on carriers in a "Ferris wheel" arrangement. The instrument must not only move the trays around the circuit, but it must also move each tray out of its carrier past a detector. Again, the passive nature of the tray requires that they all be the same in order that the instrument may handle them properly.

In U.S. Pat. No. 3,722,719 to E. Frank appears an instrument which moves trays having a two-dimensional array of tubes linearly past a carriage station. At the station, the entire row of tubes enters the carriage which transports them together to the detector. Again, for predictability, the trays all resemble each other and must fit within a particular carrier which provides them with their mode of power.

Trays carrying a multitude of items have found use in other applications as well. U.S. Pat. Nos. 2,900,074 to M. Windman; 2,919,021 to H. T. Robinson et al.; and 3,065,874 to K. M. Maiershofer show trays for carrying photographic slides in a projector. In comparison to the trays of sample tubes discussed above, the slide trays include gears which cooperate with the motor moving the trays. Furthermore, the orientation of each tray's gears helps to properly place it for the insertion of each slide into the projector's light path. Thus, the slide trays have achieved a degree of activism not seen with the sample tube-carrying trays.

SUMMARY

Providing a sample tray with position-indicating means permits it to assist the instrument in locating the sample tubes it carries. In the case of a tray having a two-dimensional array of sample holders aligned in rows, the position indicators may point out the locations of the row's centers.

The position indicators find especial utility for trays with a retaining device holding a plurality of sample holders. This type of tray finds use in an instrument which has a conveyor means to impart a force to the tray in a desired direction to move it in the same direction. The tray may then have a conveyor-cooperating section, coupled to the retaining device with the tubes, to receive the force of the conveyor and move the tray in the indicated direction.

Position indicators become particularly desirable when, in contradistinction to the slide trays alluded to above, they do not form part of the tray's conveyor cooperating device. Thus, the gears on the tray itself, where that forms a conveyor-cooperating device, does not serve to indicate the position of the tray's contents. By separating these two components, the tray's contents may have locations dictated by their own needs rather than those of the components moving the trays along their paths. Furthermore, since the position indicators locate the rows of tubes, the trays may vary from one to another; the indicators provie the instrument with the information required for it to compensate for such inconsistencies amongst trays and find the tubes.

Furthermore, the tray and the retaining device, or holder, actually carrying the tubes may constitute entirely separate and separable sections. In this fashion, each instrument will only require the number of trays that it can generally handle. This limits the expense of building these units which must have the conveyor-cooperating device, or gears. It also allows the use of the tube's original packing as the tube holder. These relatively inexpensive holders can then be discarded after each use to avoid contamination. Yet, the expensive trays find repeated service.

Lastly, the tray may have gears along both of its edges to properly distribute the instrument's motive force. Were these gears to extend all across the bottom of the tray, they would require substantial investment for their construction and could become easily damaged. However, thin gears along the tray's edges may not properly align with the wide pinion gear, for example, on the instrument itself. Accordingly, the front of the tray may have a very short section of a wide rack gear to provide the initial alignment of the tray in the instrument. Once the first gear section has achieved the proper alignment, the thinner sections will simply follow along and maintain the correct positioning of the trays.

BRIEF DESCRIPTION OF THE FIGURES

FIG. 4 gives a top plan view of two linked sample trays which can accept inserts holding a two-dimensional array of twenty sample tubes.

FIG. 5 gives a cross-sectional view along the line 5—5 of the sample tray of FIG. 4.

FIG. 6 shows a section of the front of a sample tray, rack insert, and machine readable code on the rack.

DETAILED DESCRIPTION

Figure 1:
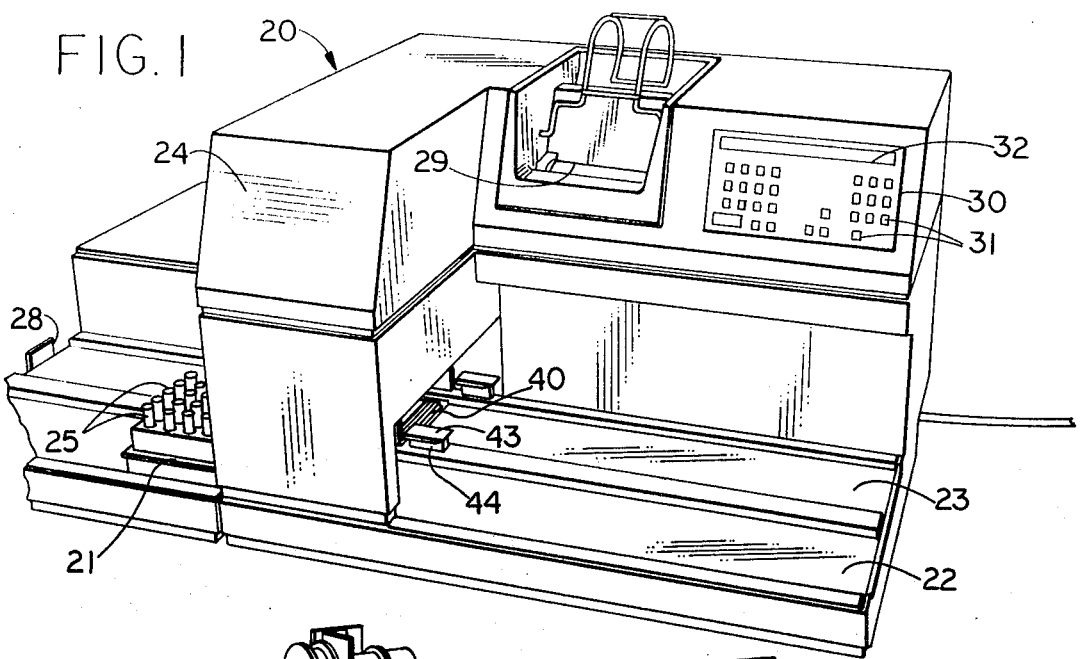
FIG. 1 gives a perspective view of a gamma counter processing sample tubes from two trains of coupled trays.

FIG. 1 shows generally at 20 a gamma counter which automatically performs assays. The samples undergoing the assays sit in a sample tray 21 moving along in either the front channel 22 or the rear channel 23.

As shown in FIG. 1, the tray 21 can move in either channel 22 or 23 from right to left. When the tray moves inside of the housing 24, the mechanism inside moves the sample tubes from the tray 21, one at a time, to a counting well to obtain a radiological analysis of the sample. The mechanism then returns the tube 25 to the sample tray 21 which then continues its travel along the path 22 or 23 to the left.

After the instrument has analyzed each of the sample tubes 25 within a tray 21, the operator may remove the tray 21 from the channel 22 or 23, as appropriate. However, should the operator not remove the sample tray 21, the instrument will continue to move additional trays through the housing 24 and push the tray 21 to the left. This can continue until the sample tray 21 abuts against the barrier 28. The barrier 38, in turn, simply prevents the sample trays from falling out of the channels 22 and 23 and off the instrument 20.

The instrument 20 also includes a printer 29 which provides a permanent report on the results of performed analyses. It also prints such information as the operator's name, the time of day, and the results of the appropriate calibarations.

Furthermore, the exterior of the instrument 20 includes the control panel 30 which incorporates the pressure sensitive keys 31 and the LED display panel 32. The keys 31 generally have dual functions. This allows them to operate in the alphanumeric mode or to permit the facile selection of particular instrumental functions. One of the keys 31 permits the selection between the two functions for the other keys.

Figure 2:
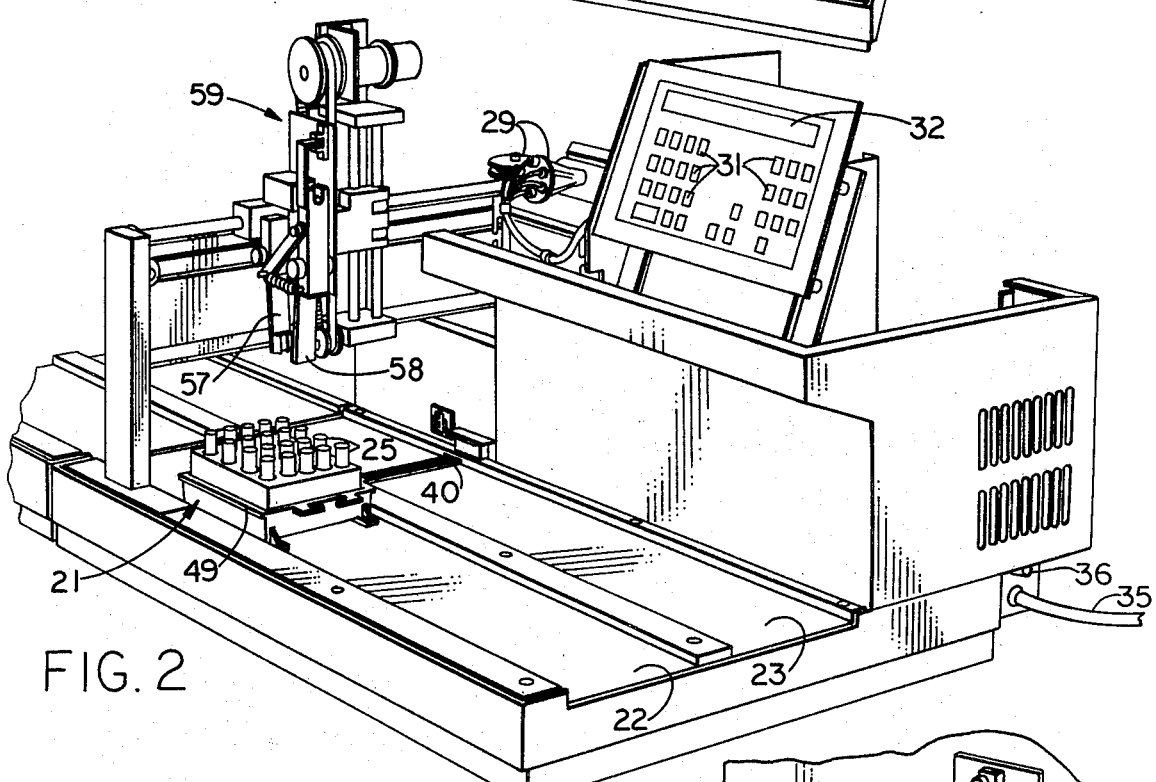
FIG. 2 provides an isometric view of the gamma counter of FIG. 1 with the cover removed to show both the conveyor mechanism for moving the trays and the transport-elevator mechanism for moving the sample tubes to the counting well.

As shown in FIG. 2, the instrument also includes a connection 35 to a power source and an on-off switch 36. Not seen in the exterior views of FIGS. 1 and 2, the instrument also has a connection to link the memory of the instrument's microprocessor with an external source. Conveniently, this may take the form of a typical RS 232 coupling.

A bar code reader 37 may have a location in front of the tray 21. There, it may obtain, through the mirror 38, information contained on the tray's front. The reader 37, when the tray moves in the channel 22, may retract upward to avoid interfering with the tray's progress. The reader 37 occupies the position shown in phantom when reading the code on a tray in the rear channel 23.

To perform an assay, the operator places the sample tray 21 with the tubes 25 on one of the paths 22 or 23. He then indicates on the switches 31 of the control panel 30 the essay he wishes to have performed as well as various pieces of information. In particular, he will inform the instrument as to whether the tray 21 sits in the front or rear channel 22 or 23.

In either event, the operator pushes the tray 21 until it abuts against the wide pinion gear 39 of the front channel 22 or the similar gear 40 of the rear channel 23. The tray 21 includes a rack gear on its lower surface which the discussion below concerning FIGS. 7, 8, and 9 indicates. With the tray 21 in contact with either of the gears 39 or 40, the remaining operation of the instrument 20 becomes automatic.

The gear 39 or 40 rotates to move the tray 21 into operational position. Motors lying below the channels 22 and 23 provide power to the gears 39 and 40, respectively.

To insure the firm engagement between the gear 39 or 40 and the tray 21, the front channel 22 includes the overhanging ledge 43 attached to the post 44. Similarly, the rear channel 23 includes the ledge 45 attached to the post 46. The ledge 43 and 45 extend sufficiently into the channels 22 and 23 to actually lie over the ridge 49 on the tray 21. In fact, as shown in FIGS. 4 to 7, the tabs 50 extend from the ridge 49 and will also lie beneath the overhanging ledge 43 or 45.

The ledge 43 or 45, when lying over the ridge 49, prevents the tray 21 from tipping upwards under the action of the moving gear 39 or 40, as appropriate. Thus, the ledges 43 and 45, by pushing downwards on the ridge 49 and the tabs 50, force the tray 21 into contact with the rotating pinion gear 39 or 40. As a result, when either or both of these gears rotates, it moves the tray into position for the assays on the samples.

To stop the gears 38 and 40, and thus the tray 21, the front channel 23 includes the sensor 54. The pinion gears 39 and 40 move a tray in the front channel 22 or the rear channel 23, respectively, until the tabs 50 (shown in FIGS. 4 to 7) interrupt the opto-sensor 53 or 54, respectively. In fact, the tabs 50 have the purpose of providing an indication through the opto-sensors 53 and 54 as to when the pinion gears 39 and 40, respectively, should stop.

Each row of tubes 25 in the tray 21 has a separate tab 50. The location of the tab will cause its relative row, when the tab interrupts the photodetector 53 or 54, to occupy the operational position where its sample tubes may travel to the counting well.

In particular, when a tab 50 interrupts the optosensor 53 or 54, a row of tubes will lie directly underneath the fingers 57 and 58. The fingers 57 and 58, in turn, couple to the transport and elevator mechanism, shown generally at 59. The fingers 57 and 58, in conjunction with the elevator-transport mechanism 59, lift a tube 25 from the tray 21, transport it to a location directly above the counting well. They then lower the tube into the well for counting. After the completion of the counting, the tube 21 is lifted out of the well, returned to a location above its original position within the tray 21, and then lowered into the tray.

Figure 3:
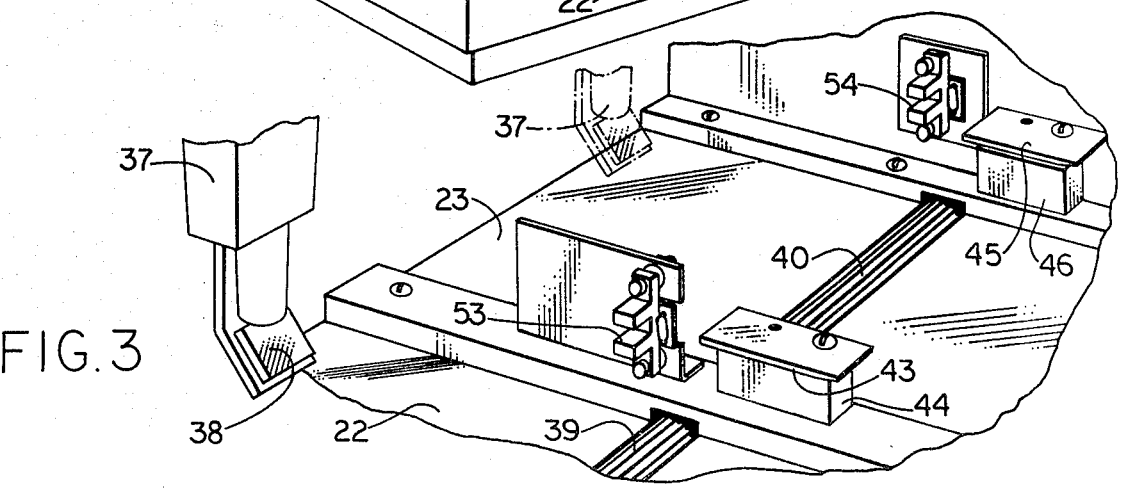
FIG. 3 gives an enlarged view of the conveyor mechanism which moves the train of linked trays and the opto-sensor which determines where to stop the trays.

As shown in FIG. 4, the tray 21 includes four rows 202 each holding five sample tubes 25. Each tab 50 corresponds to one of the rows 202. As discussed above, each tab 50, when it intercepts the optical sensor 53 or 54 in FIG. 3, causes the motor of the pinion gears 39 or 40, respectively, to stop and place one of the rows 202 of sample tubes underneath the fingers 57 and 58.

Specifically, each leading edge 203 of the tabs 50 sits at a constant distance away from the center of the row 202 to which that tab corresponds. As shown in FIG. 4, in particular, the leading edge 203 sits at a slight distance towards the front 204 of the tray 21. This offset of the leading edges 203 of the tabs 50 from the center of the rows 202 compensates for the position of the optical sensors 53 and 54 relative to the fingers 57 and 58. It also corrects for time actually required for the pinion gears 39 and 40 to come to a stop after the tabs 50 have interrupted the appropriate optical sensor.

The stopping of the tray underneath the elevator-transport mechanism 59 depends solely upon the tabs 50 attached to the tray 21. Consequently, the tray 21 may include a different number of rows than the four rows shown in FIG. 4. Thus, for example, increasing the number of rows 202 would merely involve a larger tray having additional tabs 50 on its edge. In particular, the tray may include twelve rows with the same number of tabs 50 and, correspondingly, hold 60 tubes.

Changing the number of columns 204 represents a more difficult task. The program in the instrument's microcomputer must include a subroutine that would allow it to respond to an indication that the tray has a different number than five columns. This received indication would then control the positioning of fingers 57 and 58 over the sample tubes 25.

The letters 205 on the tab 50 and on the ridge 49 on the other side of the tray inform the operator of the particular rows in which the tubes 25 sit. Similarly, the numbers 206 indicate the particular columns for the tubes.

To actually hold the tubes 25, the rack 209 sits inside of the tray 21. The opening 210 in the rack 209 serves to place the tubes 25 in their correct positions. The rack 209 may have a construction of plastic, styrofoam, cardboard, or many other materials. In particular, when made of a less expensive material, the rack 209 can constitute part of the original containers for the sample tubes 25. Disposal of a less expensive rack 209 after use prevents contamination of one rack by the radioactive contents of the sample tubes from prior assays.

The bottom 211 of the tray 21 provides a surface upon which the rack 209 sits. Since the rack 209 has its own lower surface 212, the tray's bottom 211 need not extend across the entire width of the tray. Accordingly, the opening 213 in the tray's bottom 211 saves material and expense in the tray's construction, as also seen in FIG. 5.

The front 204, the rear 215, and the two sides 216 of the tray include the ribs 217 extending into the tray's interior. The ribs 217 assure the proper positioning of the rack 209 within. The sloping tops 218 assist in the initial insertion of the rack 209 into the tray 21.

FIG. 6 shows the front end 204 of the tray 21 and the front 219 of the rack 209. The code 220 appears on the front of the rack 209 where the reader 37 of FIG. 3 can obtain its information. The data contained in the code 220 may relate to the number of columns in the rack 209, the assays that should be performed on the tubes in the rack 209, and other such information.

As discussed above with regards to FIGS. 1 through 3, the pinion gears 39 and 40 of the instrument engage rack gears on the bottom of the tray 21. These gears appear in FIGS. 7 through 9. Specifically, each tray 21 includes a long thin rack gear 223 running almost the entire length of one side of the tray and a similar long thin rack gear 224 on the other side. Lastly, the tray's bottom 211 includes a very short but wide rack gear 225 at its front surface 204. As shown in FIG. 8, the front rack gear 225 merges immediately into the side gears 223 and 224 to form, in effect, a single gear running the entire length of the tray 21. Once one of the pinion gears 39 or 40 has engaged the front rack gear 225, it will then proceed to engage properly the teeth of the side gears 223 and 224.

The wide short gear 225 has the purpose of assuring the proper alignment of the tray 21 over the pinion gear 39 or 40, as appropriate. In other words, a wide tooth of the pinion gear 39 or 40 first engages the first wide tooth 226 of the rack gear 225. Even if tray 21 has a slight misalignment relative to the pinion gear 39 or 40, the engagement between the pinion gear 39 or 40 and the first tooth 226 of the rack gear 225 will force the tray 21 into proper alignment. The pinion gear 39 or 40 will then proceed to engage the thinner rack gears 223 and 224 lying behind the front gear 225.

Conceivably, the pinion gear 39 or 40 could mesh with the rack gears 223 and 225 with a slight misalignment between them; in other words, the tray 21 would not, were this to occur, proceed perpendicularly across the pinion gear 39 or 40. However, the prior engagement of the pinion gear 39 or 40 with the wide front gear 225 has previously forced the tray 21 into proper alignment; it thus prevents any misalignment between the long, thin gears 223 and 224 with the pinion gear 39 or 40.

The front tooth 226 of the front gear 225 appears thinner than any other tooth in either the front gear 225 or the rear gears 223 and 224. This facilitates the initial engagement of the pinion gear 39 or 40 with the teeth of the tray 21.

Figure 9:
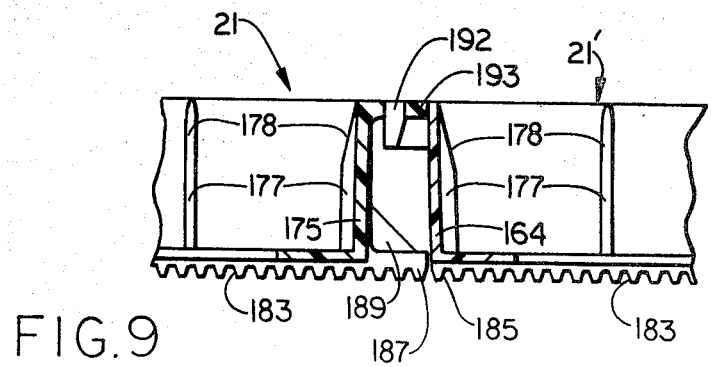
FIG. 9 has a cross-sectional view along the line 9—9 of the linked sample trays of FIG. 4 showing the coupling mechanism of the two trays.

The thin rack gears 223 and 225 also include the trailing segments 227 and 228 which extend beyond their tray's rear surface 215. As shown in FIG. 9, these extended portions create a continuous rack gear between the two coupled trays 21 and 21'. Additionally, the overhanging gear segments 227 and 228 provide the proper spacing between the bottoms of the two coupled trays 21 and 21'. The triangular stiffening sections 229 and 230 (with the latter shown in FIG. 4) provide structural rigidity to the overhanging gear segments 227 and 228, respectively.

Figure 7:
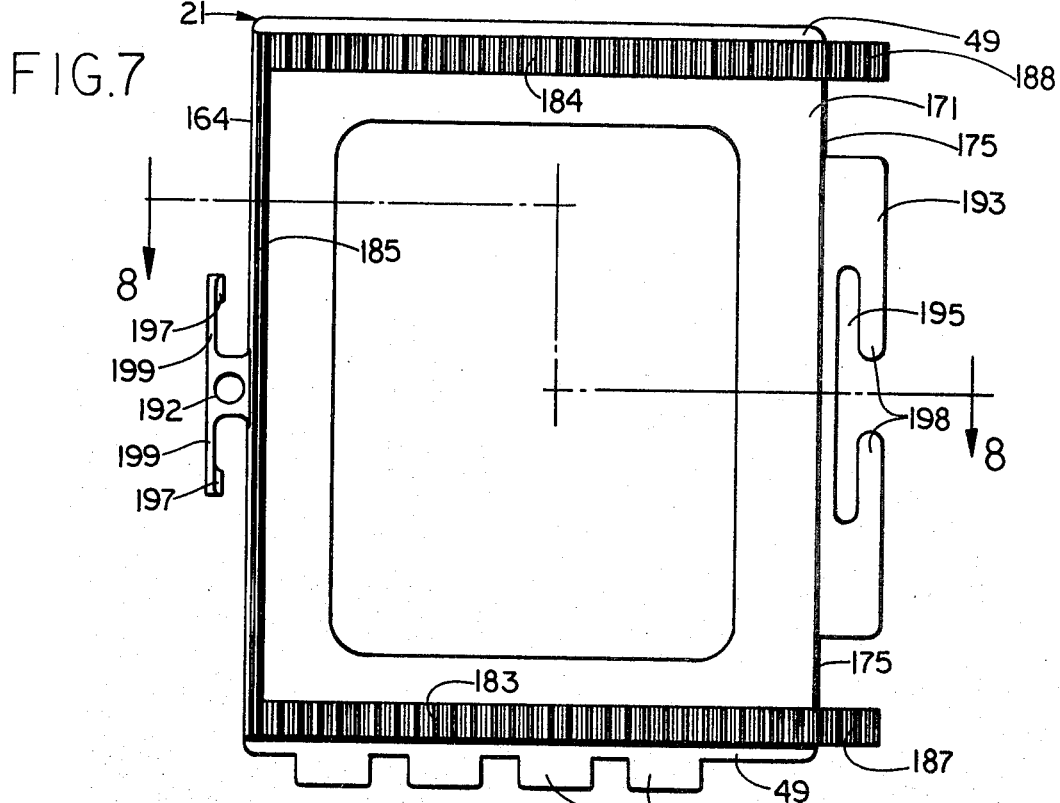
FIG. 7 gives a bottom plan view of the sample tray shown in FIGS. 4 and 5.
Figure 8:
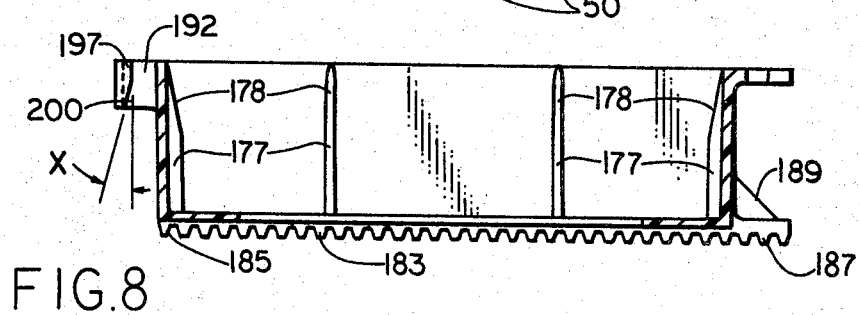
FIG. 8 provides a cross-sectional view along the broken line 8—8 of the carrier tray of FIG. 7.

For the actual coupling between trays, the tray 21 includes the T-tab 232 attached to the top of the tray's front 204, as shown in FIG. 7. The C-hook 223 attaches to the tray's rear 215. The T-tab 232, when inserted into the C-hook 233, as in FIGS. 4 and 9, connects the two trays 21 and 21' together and permits them to move as a unit. In fact, the front and rear channels 22 and 23 of the instrument in FIGS. 1 through 3 can each accomodate several trays. When several coupled trays occupy one of the channels 22 and 23, the pinion gear 39 or 40 will move all of the linked trays together as a single unit in the form of a train. The motors coupled to the gears 39 and 40 each have sufficient power to move a train of coupled trays in the channels 22 and 23.

A train of coupled trays, nonetheless, receives its power only from either pinion gear 39 or 40. Thus, regardless of the length of the tray train, it receives its power from the single point in the channel 22 or 23 where it contacts the pinion gear 39 or 40, as appropriate. Regardless of the length of the train, the instrument provides the power to it at a single point along the path of its movement. As a consequence, the operator may add additional trays at the end of the train without the threat of adversely interfering with the motive mechanism. Further, he can add the trays while the instrument performs assays on tubes from trays previously added. Moreover, the memory in the instrument's microcomputer allows the operator to indicate on the control panel 30 the assays desired for the newly added trays. And, after the instrument has completed the assays for all the tubes in a particular tray, the operator may remove that tray while the instrument continues its assays of tubes in other trays.

Furthermore, adding an additional tray to a coupled train in the channel 22 or 23 represents a simple task. As illustrated in FIG. 9, with the trays 21 and 21' coupled together, the C-hook 233 abuts directly against the front surface 224 of the following tray 21'. Thus, to add a further tray to the train, the operator holds the following tray 21' at a sufficient height above the leading tray 21 that the T-tab 232 cannot contact the C-hook 233. Since neither of the components of the coupling mechanism extends below half the tray's height, this merely requires holding the following tray 21' at about one third of the tray's height above the leading tray 21. The operator then moves the following tray 21' up against the leading tray 21 until its C-hook 233 contacts the front surface 224 of the other. Lowering the following tray 21' until it sits on the surface of the channel 22 or 23 causes the T-tab 232 to enter the opening 235 of the C-hook 233 and couple the two trays.

As shown in FIGS. 4 and 9, the C-hook 233 establishes the proper distance between the top of the two sample trays 21 and 21'. This distance corresponds to the separation established between the bottoms of these trays by the overhanging gear portions 227 and 228.

However, to assure the proper distance between the trays 21 and 21', the C-hook 233 must abut directly against the front 204 of the following tray 21'. To accomplish this objective, the T-tab 233 actually pushes the C-hook 232 against the tray's front surface 204.

In fact, as seen in FIG. 7, the width of the rear portions 238 of the C-hook 233 actually exceeds the distance between the tips 237 of the T-tab 232 and the front surface 204 of the tray 21. As a result, when the T-tab 232 enters the C-hook 235, the width of the extension 238 actually forces the tips 237 outward and away from the front 204 of the tray 21.

The resilience of the T-tab 234, in turn, causes the tips 237 to push the extensions 238 and thus the C-hook 233 back towards the front 204 of the leading tray 21. This resilient flexing of the T-tab 237 against the C-hook 233, in fact, forces the latter directly into contact with the front 204 of the tray 21.

To assist in its resilient flexing and insertion into the C-hook 235, the T-tab 232 includes the thin sections 239 adjacent to its tips 237. These thinner sections 239 more readily bend without breaking. Their resiliency forces the two trays 21 and 21' into contact with each other.

As stated above, the tips 237 of the T-tab 232 have a greater thickness than the flexing portions 239. To aid their insertion into the C-hook 235, they have the lower bevelled edges 240. Thus, insufficient room exists between the end portions 237 of the T-tab 232 to accomodate the width of the extensions 238 of the C-hook 233. Yet, the bevelled edge 240 of the T-tab 232 fits over the extensions 238 to permit the initial placement of the T-tab 232 into the opening of the C-hook 233. The continued insertion forces the thicker end portion 237 into the opening 235 and flexes the middle sections 239 of the T-tab 232.

Figure 10:
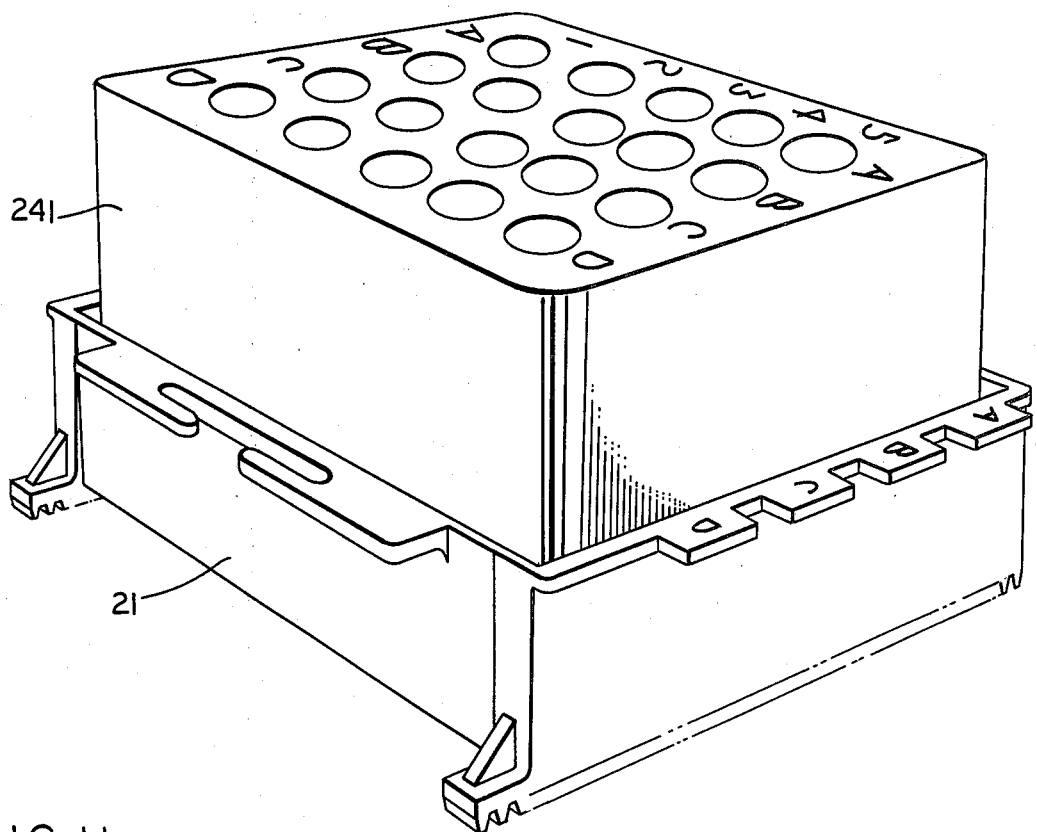
FIG. 10 shows a tray with a styrofoam insert or rack.
Figure 11:
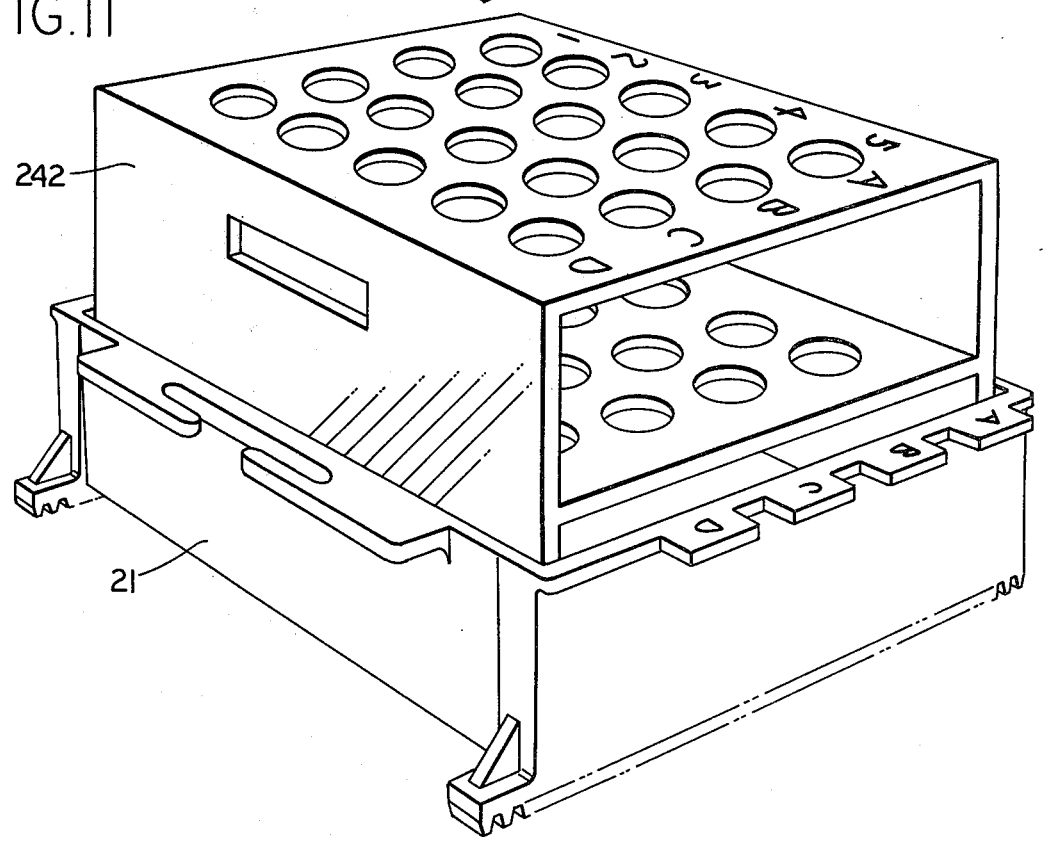
FIG. 11 has a tray with a removable plastic rack.
Figure 12:
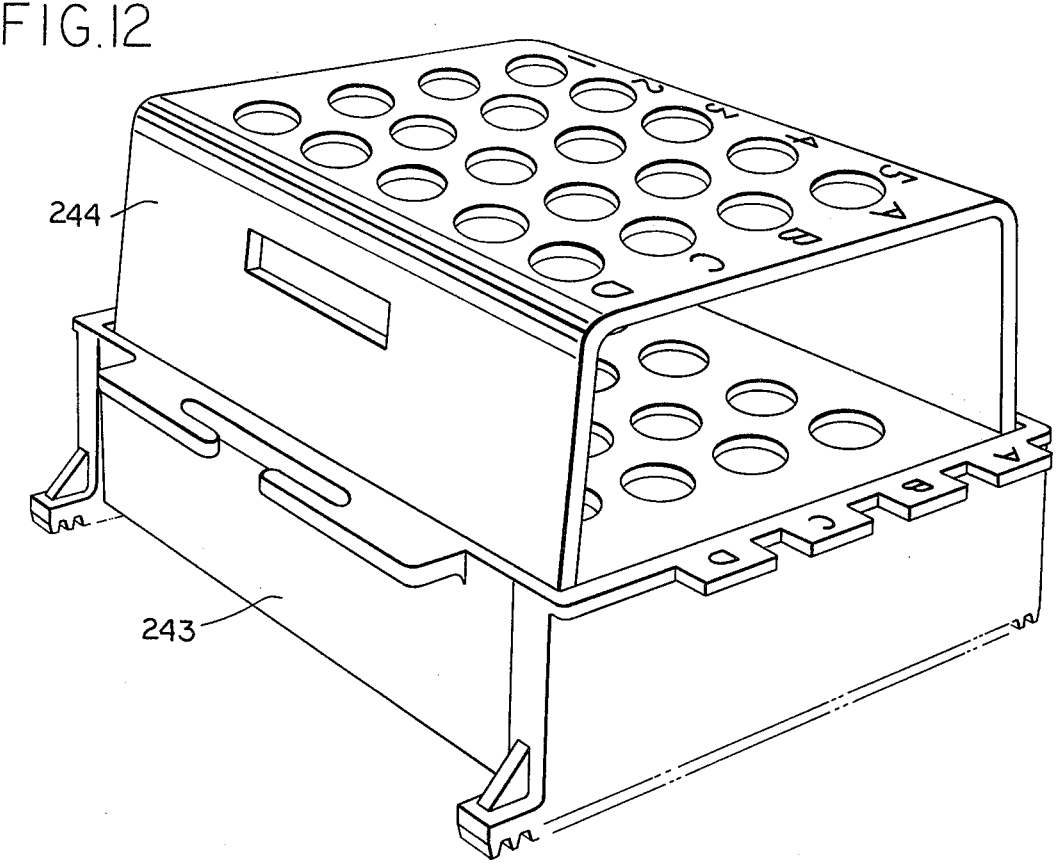
FIG. 12 portrays a tray with an integrally formed plastic holder for the sample tubes.

As suggested above, the rack 209 sitting in the tray 21 may have a construction of several materials. The actual rack 209 in FIGS. 4 and 5 has a cardboard composition. The rack 241 in FIG. 10 has a styrofoam composition while the rack 242 of FIG. 11 is formed of plastic. The racks 209, 241, and 242 of FIGS. 4, 10, and 11, respectively, interchangeably fit into the same sample tray 21. Removing one allows the insertion of another.

The tray 243 does not have a removeable rack. Rather, its rack 244 forms a permanent part of the tray. The rack portion 244 of the tray 243 may have a composition of plastic.

Accordingly, what is claimed is:

1. A sample tray for use with an analytical instrument having detector means for performing an analysis upon a sample contained in a sample holder and conveyor means for imparting a force to said tray, in a predetermined direction, said tray comprising:
   (A) retaining means for holding a plurality of said sample holders in rows and in a plane including said direction;
   (B) conveyor cooperating means, couplable to said retaining means, for receiving said force of said conveyor means to move said retaining means in said direction; and
   (C) machine-readable position-indicating means aside from printed alpha-numeric data, couplable to said retaining means and separate from said retaining means and from said conveyor cooperating means, for indicating to said instrument the location of the center of each of the rows.

2. The sample tray of claim 1 wherein said tray has a front, rear, top, and bottom and further comprising coupling means including first and second portions coupled to said front and said rear of said tray, respectively, said first portion of one sample tray being manually engageable with and disengageable from said second portion of another sample tray, said first and second portions of said one and said another trays, respectively, when engaged with each other and when said conveyor imparts to said conveyor cooperating means of said another tray sufficient force to move said one and said another trays, transmitting sufficient force to said one tray to move said one tray.

3. The sample tray of claim 2 wherein said tray includes first and second sides extending between said front and said rear and said position indicating means includes, for each of said rows, a tab extending outwardly from said first side and having a predetermined location relative to said row, each of said tabs having the same predetermined location relative to their respective rows.

4. The sample tray of claim 3 wherein each of said rows has a center and the edge of each of said tabs closer to said front of said tray is located at a predetermined distance from said center of that tab's respective row.

5. The sample tray of claim 3 wherein said tray further comprises:
   (A) a rack including said retaining means and having a bottom, four sides, and a top having openings for said sample holders;
   (B) holder means, separate from and couplable with said rack, and including said conveyor cooperating means, for retaining said rack in a fixed position relative to said conveyor cooperating means.

6. The sample tray of claim 5 wherein said holder includes a front wall, a rear wall, and first and second side walls connected to said front wall and said rear wall, said front, rear, first, and second side walls defining an interior area between them, one of said front and rear walls and one of said first and second side walls having projections attached thereto extending into said interior area.

7. The sample tray of claim 3 wherein said conveyor cooperating means includes a rack gear extending from said front of said tray to said rear of said tray and sufficiently beyond said front and said rear to form, when said first portion of said coupling means on said one tray is engaged with said second portion of said ocupling means on said another tray, a continuous rack gear from said another to said one tray.

8. The sample tray of claim 7 wherein said first and second portions of said coupling means do not extend below about the upper half of the front and back, respectively, of said sample tray.

9. The sample tray of claim 8 wherein, when said first portion of said coupling means of said one tray is engaged with said second portion of said coupling means of said another tray, said coupling means maintains a first predetermined distance between the top of said rear of said another tray and the top of said front of said one sample tray and said rack gear maintains a second predetermined distance between the bottom of said rear of said another tray and the bottom of said front of said one tray.

10. The sample tray of claim 9 wherein said first portion of said coupling means includes a tab attached to said front of said sample tray, said second portion of said coupling means includes an at least partially enclosed opening attached to said rear of said tray, into which said tab fits and, when said second portion of said coupling means of said another tray contacts said front of said one tray directly below said first portion of said coupling means of said one tray, lowering said one sample tray until said rack gears of said one and said another sample trays are at the same height, will place said tab into said opening and engage said first and second portions of said coupling means.

11. The tray of claim 10 wherein, when said second portion of said coupling means of said another tray is engaged with said first portion of said coupling means of said one tray, said first and second portions of said coupling means exert a continual pressure against each other in a direction to force said one and said another trays towards each other.

12. The sample tray of claim 7 wherein said rack gear includes:

(A) first and second sections coupled to the bottom of said tray said first and second sections being oriented from said front of said tray towards said rear of said tray, said first and second sections starting at about the same distance from said front of said tray and being simultaneously engageable with a pinion gear, said first and second sections being separated from each other by a nonzero distance; and (B) a third section having a width at least about equal to said distance between said first and second sections and located between about said front of said tray and said first and second sections, said first and second sections being located behind said third section in a position where a pinion gear, when in operation, and, after being engaged with said third section and then disengaging from said third section, immediately engages said first and second sections.

13. The sample tray of claim 12 wherein, with a plurality of said sample trays coupled together through the engagement of said first and second portions of said coupling means on said sample trays and a force sufficient to move said sample trays along a predetermined path exerted on said rack gear of the particular sample tray of said coupled-together plurality of sample trays having a first portion of said coupling means not engaged with the second portion of said coupling means of another sample tray, the remainder of said plurality of sample trays will follow along said predetermined path on a substantially smooth surface.

14. The improvement of claim 13 wherein the exterior of at least one of said first and second sides includes information thereon readable by mechanical reading means.

15. The sample tray of claim 13 wherein said tray further comprises:
(A) a rack including said retaining means and having a bottom, four sides, and a top having openings for said sample holders; and
(B) holder means, separate from and couplable with said rack and including said conveyor cooperating means, for retaining said rack in a fixed position relative to said conveyor cooperating means.

16. The sample tray of claim 15 wherein said holder means includes a front wall, a rear wall, and first and second side walls connected to said front wall and said rear wall, said front, rear, first, and second side walls defining an interior area between them, one of said front and rear walls and one of said first and second side walls having projections attached thereto extending into said interior area.

17. The sample tray of claim 3 wherein said sample tray includes first and second sides extending between said front and said rear and wherein the exterior of at least one of said sides includes information thereon readable by electromechanical reading means.

18. The sample tray of claim 17 wherein said tray further comprises:
(A) a rack including said retaining means and having a bottom, four sides, and a top having openings for said sample holders; and
(b) holder means, separate from and couplable with said rack and including said conveyor cooperating means, for retaining said rack in a fixed position relative to said conveyor cooperating means.

19. In a sample tray having a bottom, top, front, rear, and sides for use with an analytical instrument having conveyor means for imparting a force to said tray in a predetermined first direction, when said front of said tray is oriented in said first direction, said conveyor means including a pinion gear having a length at least as long as half of the width of said tray between said sides, the improvement comprising a gear having:

(A) first and second rack sections engageable with said pinion gear, coupled to the bottom of said tray, said first and second sections being oriented from said front of said tray toward said rear of said tray, the distance between said first and second sections being less than said length of said pinion gear, said first and second sections starting at about the same distance from said front of said tray and being simultaneously engageable with said pinion gear; and (B) a third section, engageable with said pinion gear, having a width at least about equal to the distance between said first and second sections, and located between about said front of said tray and said first and second sections, said first and second sections being located behind said third section in a position where said pinion gear when, in operation, disengaging said third section immediately engages said first and second sections.

20. The improvement of claim 19 wherein said tray has a front, rear, top, and bottom and further comprising coupling means including first and second portions coupled to said front and said rear of said tray, respectively, said first portion of one sample tray being engageable with said second portion of another sample tray, said first and second portions of said one and said another trays, respectively, when engaged with each other and when said conveyor imparts to said conveyor cooperating means of said another tray sufficient force to move said one and said another trays, transmitting sufficient force to said one tray to move said one tray and, when said first portion of said one tray is engaged with said second portion of said another tray, said coupling means maintains a first predetermined distance between the top of the rear of said another sample tray and the top of the front of said one sample tray and said rack gear maintains a second predetermined distance between the bottom of the rear of said another sample tray and the bottom of the front of said one sample tray.

21. The improvement of claim 20 wherein said rack gear extends from said front of said tray to said rear of said tray and sufficiently beyond said front and said rear to form, when said first portion of said coupling means of said one tray is engaged with said second portion of said coupling means on said another tray, a continuous rack gear from said another tray to said one tray.

22. The improvement of claim 21 wherein, when said second portion of said coupling means of said another tray is engaged with said first portion of said coupling means of said one tray, said first and second portions of said coupling means exert a continual pressure against each other in a direction to force said one and said another trays towards each other.

23. The improvement of claim 22 wherein said first portion of said coupling means includes a tab attached to said front of said sample tray, said second portion of said coupling means includes an at least partially enclosed opening, attached to said rear of said tray, into which said tab fits and, when said second portion of said coupling means of said another tray contacts said front of said one tray directly below said first portion of said coupling means of said one tray, lowering said one sample tray until said rack gears of said one and said another sample trays are at the same height will place said tab into said opening and engage said first and said second portions of said coupling means.

24. In a sample tray having a front, rear, sides coupled to said front and rear, top, and bottom for use with an analytical instrument having conveyor means for imparting a force to said tray in a predetermined direction when said front of said tray is oriented in said direction, said tray including conveyor cooperating means for receiving said force of said conveyor means to move said tray in said direction, the improvement comprising coupling means including first and second portions, coupled to said front and rear of said tray, respectively, said first portion of one tray being manually engageable with and disengageable from said second portion of another tray, said first and second portions of said coupling means of said sample tray not extending below about the upper half of the front and back, respectively, of said tray, one of said first and second portions extending a predetermined distance beyond the front or rear, respectively, of a first tray, said predetermined distance being such that when the back or front, respectively, of a second tray abuts against said one portion with the sides of said first and second trays falling generally in a line, relative vertical motion of said second tray will bring said first and second portion of said first and second trays into engagement.

25. The improvement of claim 24 wherein said first and second portions of said one and another trays, respectively, when engaged and when said conveyor imparts to said conveyor cooperating means of said another tray sufficient force to move said one and said another trays, transmit sufficient force to said one tray to move said one tray, and wherein said one portion is said second portion and extends beyond the rear of said first tray and, when the front of said second tray abuts against said second portion, with the sides of said first and second trays falling generally in a line, downward motion of said second tray relative to said first tray will bring said first and second portions of said second and first trays, respectively, into engagement.

26. In a sample tray having a front, rear, top, and bottom for use with an analytical instrument having conveyor means for imparting a force to said tray in a predetermined direction when said front of said tray is oriented in said direction, the improvement comprising (a) conveyor cooperating means for receiving said force of said conveyor means to move said tray in said direction, said conveyor cooperating means including a rack gear extending from said front of said tray to said rear of said tray, and (b) coupling means including first and second portions, coupled to said front and rear of said tray, respectively, said first and second portions of said one and another trays, respectively, when engaged and when said conveyor imparts to said conveyor cooperating means of said another tray sufficient force to move said one and said another trays, transmitting sufficient force to said one tray to move said one tray, said rack gear extending sufficiently beyond said front and rear to form, when said first portion of said coupling means on said one tray is engaged with said second portion of said coupling means on said another tray, a continuous rack gear from said another tray to said one tray.

27. The improvement of claim 26 wherein, when said first portion of said coupling means of said one tray is engaged with said second portion of said coupling means of said another tray, said coupling means maintains a first predetermined distance between the top of said rear of said another tray and the top of said front of said one tray and said rack gear maintains a second predetermined distance between the bottom of said rear of said another tray and the bottom of said front of said one tray.

28. A sample tray for use with an analytical instrument having detector means for performing an analysis upon a sample contained in a sample holder and conveyor means for imparting a force to said tray in a predetermined direction, said tray comprising:
(A) a rack including a bottom for supporting a plurality of said sample holders and retaining means, coupled to said bottom, for holding said plurality of said sample holders in rows and in a plane including said direction; and
(B) holder means, separate from and coupable with said rack, including (a) conveyor cooperating means for receiving said force of said conveyor means and (b) receiver means, coupled to said conveyor cooperating means, for retaining said rack in a fixed position relative to said conveyor cooperating means, said holder means including machine-readable position-indicating means aside from alpha numeric data couplable to and separate from said conveyor cooperating means for indicating to said instrument the location of the center of each of the rows.

29. The sample tray of claim 28 wherein said holder means includes a front wall, a rear wall, and first and second side walls connected to said front wall and said rear wall, said front, rear, first, and second side walls defining an interior area between them, one of said front and rear walls and one of said first and second side walls having projections attached thereto extending into said interior area.

30. The sample tray of claim 29 wherein said rack is formed from substantially rigid plastic.

31. The sample tray of claim 29 wherein said holder means further comprises coupling means including first and second portions coupled to said front and said rear of said holder means, respectively, said first portion of one tray being engageable with said second portion of another tray, said first and second portions of said one and said another trays, respectively, when engaged and when said conveyor imparts to said conveyor cooperating means of said another tray sufficient force to move said one and said another trays, transmits sufficient force to said one tray to move said one tray.

32. The sample tray of claim 31 wherein said holder means further includes position indicating means, includes, for each of said rows of said rack, a tab extending outwardly from said first side wall and having, when said receiver means retains said rack, a predetermined location relative to said row, each of said tabs having the same predetermined location relative to their respective rows.

33. A sample tray for use with an analytical instrument having detector means for performing an analysis upon a sample contained in a sample holder and conveyor means for imparting a force to said tray in a predetermined direction, said tray comprising:
(A) retaining means having a front, rear, and first and second sides extending between said front and rear for holding a plurality of said sample holders in rows with each of said rows having a center and in a plane including said direction;
(B) conveyor cooperating means, couplable to said retaining means, for receiving said force of said conveyor means to move said retaining means in said direction; and
(C) for each of said rows, a tab extending outwardly from said first side, the edge of each of said tabs closer to said front of said tray being located at a predetermined distance from said center of that tab's respective row.

* * * * *